United States Patent [19]

Lai et al.

[11] Patent Number: 4,466,916

[45] Date of Patent: Aug. 21, 1984

[54] SUBSTITUTED 2-KETO-1,4-DIAZACYCLOALKANES

[75] Inventors: John T. Lai, Broadview Heights; Pyong N. Son, Akron, both of Ohio

[73] Assignee: The B. F. Goodrich Company, Akron, Ohio

[21] Appl. No.: 274,586

[22] Filed: Jun. 17, 1982

Related U.S. Application Data

[60] Division of Ser. No. 88,484, Oct. 26, 1979, Pat. No. 4,292,240, which is a continuation-in-part of Ser. No. 835,065, Sep. 21, 1977, Pat. No. 4,190,571.

[51] Int. Cl.$^3$ .................. C07D 401/12; C07D 403/12
[52] U.S. Cl. .............................. 260/239.3 R; 544/231; 544/349; 544/354; 260/239.3 B; 260/239.3 P; 260/239.3 T; 544/383; 544/384; 544/313
[58] Field of Search ....................... 544/231, 349, 354; 260/239.3 R

[56] References Cited

U.S. PATENT DOCUMENTS 4,292,240  9/1981  Lai et al. ............................. 544/231

Primary Examiner—Robert T. Bond
Attorney, Agent, or Firm—Alfred D. Lobo; J. Hughes Powell, Jr.; Alan A. Csontos

[57] ABSTRACT

Novel polysubstituted 2-keto-1,4-diazacycloalkanes are powerful stabilizers for materials subject to ultraviolet (UV) light degradation, particularly for polyolefins. The cyclic 2-keto compounds of this invention have (a) a fixed two-carbon bridge between the $N^1$ and $N^4$ atoms of the diaza ring, the remaining portion of the ring having a variable length bridge of two or more carbon atoms, (b) and N-adjacent carbonyl in the fixed two-carbon bridge, and (c) at least one $N^4$-adjacent carbon atom of the diaza ring is polysubstituted, that is, has two substituents which may be cyclizable.

Compositions containing (a) the polysubstituted 2-keto-1,4-diazacycloalkanes of this invention, and (b) prior art polysubstituted 2-keto-1,4-diazacycloalkanes, exhibit excellent stability to UV light.

5 Claims, No Drawings

SUBSTITUTED 2-KETO-1,4-DIAZACYCLOALKANES

CROSS-REFERENCE TO RELATED APPLICATION

This is a division of application Ser. No. 088,484 filed Oct. 26, 1979 now U.S. Pat. No. 4,292,240 which is a continuation-in-part application of Ser. No. 835,065 filed Sept. 21, 1977, now U.S. Pat. No. 4,190,571.

BACKGROUND OF THE INVENTION

Any material, whether natural or synthetic, must exhibit satisfactory resistance to degradation under conditions of use, if products made from the materials are to find a lasting market. A lack of satisfactory resistance to degradation usually manifests itself as a partial or total loss of structural integrity, a darkening or discoloration of the product, a loss of flexibility or resilience, or a combination of the above phenomena. These phenomena are promoted or catalyzed by air (oxygen), heat and light, particularly ultraviolet light.

To protect materials, ingredients which can be collectively called stabilizers are admixed with the materials to prevent or inhibit degradation. These stabilizers work in diverse and complex ways, such that a compound which stabilizes against heat and oxygen degradation in a material may not stabilize against light degradation in the same material, or vice versa. Furthermore, a compound which acts as a stabilizer against oxygen degradation in one type of material may be relatively inactive in another type of material. Thus compounds which are stabilizers are further classed as antioxidants, antiozonants, heat stabilizers and ultraviolet (UV) light stabilizers, depending upon what type of activity and stabilization they demonstrate. In many cases, to obtain optimum protection, a mixture of compounds, each specifically selected to afford maximum protection against a certain type of degradation, is often used. In some instances stabilizers are deliberately chosen to counter the adverse effects of a plasticizer which, though highly effective as a plasticizer, tends to accelerate UV degradation. In other words, the plasticized material is more susceptible to degradation than if no plasticizer was added. As a general empirical rule, it is found that plasticizers are marginally effective as stabilizers, and stabilizers are marginally effective as plasticizers, it being more likely that a compound with desirable stabilizer properties has undesirable plasticizer properties, and vice versa.

The present invention is directed to (a) novel UV light stabilizers classed as hindered amines, more specifically classed as hindered cyclic ketodiazaalkanes, and (b) novel compositions in which the cyclic ketodiazacycloalkanes are incorporated. The basic structure of these novel compounds is a polysubstituted 2-keto-1,4-diazacycloalkane having (a) fixed two-carbon bridge between the two N atoms (the $N^1$ and $N^4$ atoms) of the diaza ring, the remaining portion of the ring having a variable length bridge of two or more carbon atoms, (b) an $N^1$-adjacent carbonyl in the fixed two-carbon bridge, and (c) at least the $N^4$-adjacent carbon atom of the fixed two-carbon bridge has two substituents (hence "polysubstituted"), which may be cyclizable, that is, form a cyclic substituent. These compounds which may be monocyclic, or with cyclizable substituents, may be bicyclic or tricyclic, are particularly useful as UV light stabilizers in substantially colorless organic materials. They may also form dimers and bis-compounds. The diaza ring of the basic structure may have from 6 to 9 ring members, more preferably from 6 to 8 ring members, and most preferably from 6 to 7 ring members.

It is known that 4,4,6,6-tetramethyl-1,5-diazacycloheptan-2-one may be prepared by a Schmidt's rearrangement of a six-membered ring with sodium azide (see German Pat. No. 2,428,877) but there is no known manner of similarly arriving at a six-membered 1,4-diaza ring with an $N^1$-adjacent carbonyl. It is also known that 1,4-diaza[3,3,5,5,]dipentamethylene-2-one may be prepared, starting with cyclohexanone, by cyclization of bis(1-cyanocyclohexyl)amine, reducing with lithium aluminum hydride to form 1,4-diaza 3,3,5,5-dipentamethylene-2-imino, treating with acetic anhydride and heating with hydrochloric acid. This is set out in greater detail in an article by Helmut Egg in Monatshefto fur Chemie 106, 1167–1173 (1975). However, starting with acetone instead of cyclohexanone, the reactions do not proceed in an analogous manner to give 3,3,5,5-tetramethyl-piperazin-2-one, as indicated by R. Sudo and S. Ichihara in "Bull. Che. Soc. Japan", 36, (1963). The Egg reference teaches substituted piperazines wherein each symmetrical $N^4$ adjacent carbon is part of a six-membered ring and the cyclic substituent on each $N^4$ adjacent carbon is always the same. A single cyclic substituent on the $N^4$ adjacent C atom of the fixed two-carbon bridge cannot be prepared by following the techniques of Egg.

Cis-3,3-dimethyl-decahydroquinoxalin-2-one has been prepared by Bindler, J. in U.S. Pat. No. 2,920,077 from difficulty obtained cis-1,2-diaminocyclohexane and it is disclosed that the cis-compounds are valuable intermediates for the production of pharmaceuticals, textile auxiliary products and synthetic materials. This reference states that the trans-1,2-diaminocyclohexane is converted with excess chloroacetic acid, or with salts thereof, into 1,2-diaminocyclohexane-N,N'-tetraacetic acid, which is quite unlike the behavior of the cis starting material. The cis-2-keto-1,4-diazacycloalkane is prepared by reacting an aqueous solution of cis-1,2-diaminocyclohexane with acetone cyanohydrin, and heating the reaction solution to dryness. The reference does not teach formation of a trans-5,6-polyalkylene-2-keto-diazacycloalkane, and there is no suggestion as to how it could be made. Nevertheless we have found that trans-2-keto-1,4-diazacyclohexane can be formed in a manner analogous to that in which the cis-2-keto-1,4-diazacyclohexane is formed.

Following the teachings of Bindler, ethylene diamine may be substituted for cyclohexanedimine and 3,3-dimethyl-2-ketopiperazine is obtained. However, when substituted ethylene diamine is used, the substituents appear on the No. 6 carbon of the diaza ring. For example, with 1,2-propane diamine, 3,3,6-trimethyl-2-ketopiperazine is formed, and with 2-methyl-1,2-propane diamine the compound obtained is 3,3,6,6-tetramethyl-2-ketopiperazine. 6-substituted and 3-substituted carbons are not symmetrical carbon atoms about the same N-adjacent atom in the diaza ring (hereinafter referred to as "symmetrical N-adjacent C atoms"). These compounds are quite unlike the novel compounds claimed. Moreover, 3,3,6,6-tetraalkyl substituted diazacycloalkan-2-ones are relatively ineffective UV stabilizers, confirming our experiences that the more substituents on symmetrical N-adjacent C atoms, the better the stabilization effect.

It is known that 2,2,4-trimethyl-tetrahydroquinoline can be hydrogenated to form a mixture of cis and trans 2,2,4-trimethyldecahydroquinoline, and, in general, the trans isomer is the major constituent. However, 2,2-dimethyl-tetrahydroquinoxaline is not hydrogenated in an analogous manner. Quite unexpectedly, providing a 2-keto substituent and forming an amide which is not generally easily hydrogenated, allows the 3,3-dimethyl-tetrahydroquinoxalin-2-one to be hydrogenated to pure cis-3,3-dimethyl-decahydroquinoxalin-2-one which, when blended into a substantially colorless organic material or carrier provides a UV light absorbing composition which is stable.

It is also known that tetraalkyl substituted piperazinediones disclosed in U.S. Pat. No. 3,920,659, are useful UV light stabilizers; in these stabilizers each of two $N^4$-adjacent symmetrical C atoms have dialkyl substituents. These compounds can be reduced to the tetraalkyl substituted piperazine as disclosed in U.S. patent application Ser. No. 239,350 (Ger. Offen. 2,315,042). There is no suggestion, however, as to how a mono-keto structure, that is a 2-keto1,4-diazacycloalkane structure may be prepared with a total of two or more substituents on symmetrical $N^4$-adjacent carbon atoms.

In addition to the tetraalkyl substituted piperazines mentioned hereinabove, it is known that tricyclo-1,4-diazaalkanes and diketo-tricyclo-1,4-diazaalkanes are good stabilizers. However, the efficacy of polysubstituted bicyclo-1,4-diazaalkanes and 2-keto-bicyclo-1,4-diazaalkanes as UV stabilizers in light absorbing, substantially colorless organic substrates, was not known, since these 1,4-diazacycloalkanes and 1,4-diazacycloalkanones were not readily available, and therefore not tested.

SUMMARY OF THE INVENTION

UV-light-stable compositions have been discovered in which an organic material or compound consisting essentially of a polyhydrocarbon, polyester, polyester resin, polyamide, vinyl polymer, cellulose ether or cellulose ester, has dispersed therein, preferably uniformly, an effective amount of 1,4-diazacycloalkan-2-one UV light absorbing compound.

More specifically, novel UV-light-stable compositions have been discovered in which the stabilizers are polysubstituted cyclic 2-keto-1,4-diazaalkanes having (a) a fixed two-carbon bridge between the N atoms of the diaza ring, the remaining portion of the ring having a bridge of variable length comprising from two to about four carbon atoms, (b) an $N^1$-adjacent carbonyl in the fixed two-carbon bridge, and (c) the $N^4$-adjacent carbon atom of the fixed two-carbon bridge has two substituents which may be cyclizable.

Though desirable stabilization of an organic material may be obtained with two substituents on the $N^4$-adjacent C atom of the fixed two-carbon bridge of a 2-keto-diazacycloalkane, it has been discovered that additional substituents, including at least one particularly on the $N^4$-adjacent C atom of the variable length bridge, provides superior UV-light-stability.

It has further been found that, in addition to UV-light compositions which include aforementioned polysubstituted 2-keto-1,4-diazamonocycloalkanes, excellent UV light stability may also be obtained with polysubstituted 2-keto-1,4-diazapolycycloalkanes, all of which are preferably used in the range from about 0.1–1 part stabilizer per 100 parts of compound subject to UV degradation.

It is therefore an object of this invention also to provide a UV-light-stable composition in which is uniformly dispersed a 2-keto-1,4-diazapolycycloalkane having two substituents which may be cyclizable, on the $N^4$-adjacent C atom in the fixed bridge; and more preferably, having a total of at least three substituents on the symmetrical $N^4$-adjacent C atoms, some of which substituents together with the C atoms to which they are bound, may be cyclizable.

In addition to the foregoing novel compositions, novel cyclic hindered amine compounds have been discovered which imbue an organic material with exceptional UV light stability, and these cyclid hindered amines are 2-keto-1,4-diazacycloalkanes having (a) a fixed two-carbon bridge between the N atoms of the diaza ring, the remaining portion of the ring having a bridge of variable length comprising from two to about four carbon atoms, (b) an $N^1$-adjacent carbonyl in the fixed bridge and (c) the $N^4$-adjacent carbon of the fixed bridge has two substituents, which may be cyclizable, and the $N^4$-adjacent carbon of the variable length bridges has at least one substituent.

More specifically, novel substituted 2-keto-1,4 diazacycloalkanes have been discovered in which (a) the symmetrical $N^4$-adjacent C atoms have a total of at least three acyclic substituents, or (b) only the $N^4$-adjacent C atom of the fixed bridge has a cyclic substituent, or (c) each $N^4$-adjacent C atom has a different cyclic substituent, or (d) the foregoing substituents are combined.

It is therefore a general object of this invention to provide novel polysubstituted 2-keto-1,4-diazacycloalkanes in which one or more diaza ring carbon atoms are disubstituted with alkyl substituents, or substituents, which together with the C atom or atoms to which they are bound, are cyclizable; or in which only the $N^4$-adjacent C atom of the fixed bridge has a cyclic substituent; or in which each $N^4$-adjacent atom has different substituents whether cyclic or acyclic; and, to provide organic compositions in which a minor amount, generally less than 1 percent by weight, of a polysubstituted 2-keto-1,4-diazacycloalkane, provides remarkable UV light stability even compared to known highly-regarded UV stabilizers.

DETAILED DESCRIPTION OF PREFERRED EMBODIMENTS

Polysubstituted (hereinafter referred to as "substituted" for brevity) 2-keto-1,4-diazacycloalkanes, in which at least the $N^4$-adjacent C atom of the fixed two-carbon bridge has two substituents whch may be cyclizable, when incorporated into UV light-degradable organic materials, exhibit a surprisingly powerful stabilizing effect. The stabilizers are used in the range from about 0.01 to about 5 parts by weight, and preferably from about 0.1 to about 1.0 part per 100 parts of organic material subject to UV light. Compositions which include these stabilizers are conveniently and economically prepared. The UV stabilizing effect of these compounds, substantially disappears when each carbon of the diaza ring is unsubstituted, and the stabilizing effect is too slight to be practical even when each symmetrical $N^4$-adjacent C atom is monosubstituted. In fact, when the 2-keto-1,4-diazacycloalkane is a six-membered ring, this lack of a practical level of UV stability is manifest when the $N^4$-adjacent C atom of the fixed, two-carbon bridge is not disubstituted or does not have a cyclic substituent. It is therefore essential for good stability, that the N⁴-adjacent C atom of the fixed two-carbon bridge be disubstituted, or have a cyclic substituent, irrespective of the number of members in the 2-keto diaza ring. It is preferred, for superior UV stabilizing performance, that some substituents on the 2-keto diaza ring be cyclizable so as to provide a diazapolycycloalkane, such as a diazabicycloalkane or diazatricycloalkane. It is more preferred that the stabilizer compounds be bicycloalkanes having six, seven, or eight membered 1,4-diaza rings, and that the N⁴-adjacent carbon of the fixed two-carbon bridge be disubstituted with acyclic substituents. The variable length bridge has two or more C atoms and may have substituents on one or more of the C atoms of the variable length bridge, and these substituents may be cyclizable.

Compositions of this invention contain 2-keto-1,4-diazacycloalkanes having the structural formula and dimers and bis compounds thereof:

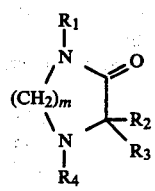 (I)

wherein, m represents an integer in the range from 2 to 7, being the number of methylene groups forming a bridge of variable length, and some of which groups (a) together with the carbons to which they are bound, may form a cyclopentyl, cyclohexyl or cycloheptyl endo ring, or (b) be substituted; when m is 2 then (I) represents a substituted 2-keto-piperazine, and when m is 6 and cyclized then (I) typically represents a substituted 2-keto-decahydroquinoxaline;

$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether groups having from 3 to about 18 carbon atoms, hydroxyalkyl ether or cyanoalkyl ether groups having from 4 to about 18 carbon atoms, alkenyl and aralkyl having from 7 to about 14 carbon atoms, alkylene having from 1 to about 7 carbon atoms and optionally containing a phosphite, ester or hindered phenol group; $R_4$ may be oxygen; and $R_2$ and $R_3$ on the N⁴-adjacent carbon of the fixed two-carbon bridge independently each represent alkyl having from 1 to about 12 carbon atoms, haloalkyl having from 1 to about 12 carbon atoms, cyanoalkyl having from 2 to about 12 carbon atoms, aminoalkyl or iminoalkyl having from 2 to about 12 carbon atoms, cycloalkyl having from 5 to about 14 carbon atoms, hydroxy-cycloalkyl having from 5 to about 14 carbon atoms, alkenyl and aralkyl having from 7 to about 14 carbon atoms, alkylene having from 1 to about 7 carbon atoms and optionally containing a phosphite, ester or hindered phenol group, and which in combination, one with another, represent cycloalkyl having from 5 to about 14 carbon atoms at least four of which are cyclized and optionally containing a keto, ester, amide, ether, thio or hydroxy group; said bis compounds consisting essentially of two 2-keto-1,4-diazacycloalkane moieties connected through each 1-position of each moiety, or each 4-position of each moiety via a bivalent radical structure selected from the group consisting of a bivalent alkyl structure and the structure

wherein G is —O—, —S—, NH, 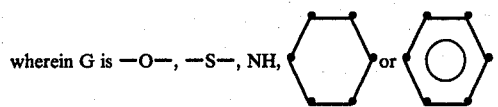

and y and z are individually an integer from 1 to about 6.

When the compositions of this invention include a stabilizer compound having a substituted alkylene group in the variable length bridge of the above-identified structural formula (I), the compound may be represented by a structural formula selected from

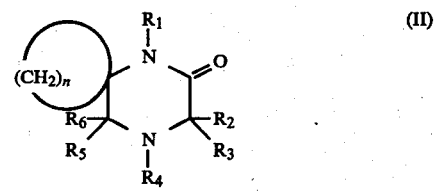 (II)

and,

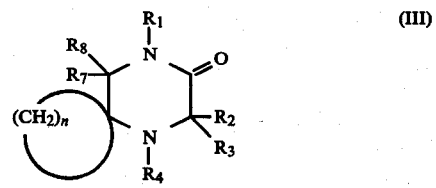 (III)

wherein n represents an integer in the range from 0 to about 6; so when n is 0 then (II) and (III) represent substituted 2-keto-piperazine, and when n is 4 with the variable length bridge cyclized, then (II) and (III) represent 2-keto-decahydroquinoxaline; and $R_5$, $R_6$, $R_7$, $R_8$ in the variable length bridge have the same connotation as $R_2$ and $R_3$ in (I) hereinabove, and additionally may be H, except that $R_5$ and $R_6$ are different if either is H; $R_2$, $R_3$ may be cyclizable, as may be $R_5$, $R_6$ and $R_7$, $R_8$; and, if cyclized, the cyclic substituents may be the same or different.

Illustrative of the type of substituents that are effectual in the above-identified 2-keto-diazacycloalkanes II and III are:

where $R_1$ and/or $R_4$ is alkyl, examples are methyl, ethyl, n-propyl, n-butyl, t-butyl, N-nexyl, n-octyl, 2-ethylhexyl, n-decyl, n-tetradecyl, n-octyldecyl, and the like;

where $R_1$ and/or $R_4$ is hydroxyalkyl, examples are 2-hydroxyethyl, 2-hydroxypropyl, 3-hydroxypropyl, 2-hydroxybutyl, 6-hydroxyhexyl, 8-hydroxyoctyl, and the like;

where $R_1$ and/or $R_4$ is haloalkyl, examples are 2-chloroethyl, 2-bromoethyl, 2-fluoroethyl, 2-chlorobutyl, 4-chlorobutyl, 2-chloroethylhexyl, and the like;

where $R_1$ and/or $R_4$ is cyanoalkyl, examples are 2-cyanoethyl, 3-cyanopropyl, 4-cyanobutyl, 8-cyanooctyl, and the like;

where $R_1$ and/or $R_4$ is aminoalkyl or iminoalkyl, examples are 2-aminoethyl, 3-aminopropyl, 4-aminobutyl, 6-aminohexyl, 2-methyl-2-aminoethyl, and the like;

where $R_1$ and/or $R_4$ is ether, examples are methoxyethyl, ethoxyethyl, ethoxypropyl, octyloxyethyl, phenoxyethyl, p-methyl-phenoxypropyl, and the like;

where $R_1$ and/or $R_4$ is hydroxyalkylether or cyanoalkylether, examples are 2-hydroxyethyloxaethyl, p-(2-hydroxypropyl)-phenyloxapropyl, 4-hydroxybutyloxahexyl, 2-cyanoethyloxaethyl, 2-hydroxyethyl-di(oxaethyl), and the like;

For $R_2$, $R_3$, $R_5$, $R_6$, $R_7$ and $R_8$, examples are methyl ethyl, propyl, n-butyl, isobutyl, n-hexyl, 2-ethylheptyl, n-decyl, and where the substituents are cyclizable, cyclopentyl, methylcyclopentyl, cyclohexyl, methylcyclohexyl, dimethyl cycloheptyl, piperidyl, 2-2',6-6'-tetramethyl piperidyl, and the like.

Novel compounds of this invention are those represented by formulae I, II, and III wherein: n represents an integer in the range from 1 to about 5 so as to have a carbon bridge of variable length having at least 2 carbon atoms bridging may form a cyclopentyl, cyclohexyl or cycloheptyl ring;

$R_1$ and $R_4$ have the same connotation as in (I), (II) and (III) hereinabove;

$R_2$, $R_3$, $R_5$, $R_6$, $R_7$ and $R_8$ each independently represents an acyclic substituent and $R_2$, $R_3$ are different from $R_5$, $R_6$;

$R_2$, $R_3$ may be cyclizable, as may be $R_5$, $R_6$, and $R_7$, $R_8$, and the cyclic substituents $R_2$, $R_3$ and $R_5$, $R_6$ are different;

$R_2$, $R_3$ may be cyclizable and $R_5$, $R_6$, $R_7$, $R_8$ may each independently represent an acyclic substituent.

Examples of specific novel substituted mono-ketodiazacycloalkan-2-ones wherein $N^4$-adjacent C atom of the fixed two-carbon bridge has two substituents which may be cyclizable, are:

(a) diazamonocycloalkan-2-ones having a total of more than four substituents on the diaza ring, for example, 3,3,5,5,6-pentaalkyl-1,4-piperazin-2-one;

(b) trans-1,4-diazabicycloalkan-2-ones, for example, trans-3,3-dialkyl-decahydroquinoxalin-2-one; and, (c) mono keto-diazatricycloalkan-2-ones, for example, 3,3-($\beta,\beta'$-ditert-butyl amine)decahydroquinoxalin-2-one.

The more preferred substituted 2-keto-1,4-diazacycloalkane compounds are those wherein $R_1$ and/or $R_4$ is alkyl having from 4 to 18 carbon atoms, benzyl, cyclohexylmethyl, hydroxyalkyl having from 1 to about 6 carbon atoms, hydroxyalkyl ether having from 4 to about 12 carbon atoms, cyanoalkyl having from 2 to about 6 carbon atoms, and aminoalkyl having from 1 to about 6 carbon atoms; $R_2$, $R_3$, $R_5$, $R_6$, $R_7$, and $R_8$ are alkyl having from 1 to about 12 carbon atoms, or polymethylene having from 5 to 6 carbon atoms which are cyclizable; only $R_2$, $R_3$ may be cyclized, or $R_2$, $R_3$ and $R_5$, $R_6$ may be cyclized, and if $R_2$, $R_3$, and $R_5$, $R_6$ are each cyclized, the cyclic substituents are different; and n is a numeral in the range from 4 to about 6 when the methylene groups are cyclized.

Examples of the aforespecified more preferred substituted mono-keto-diazaalkan-2-ones are:

$N^4$-($\beta$-hydroxyethyl)-3,3,6-trimethyl-piperazine-2-one;

$N^4$-($\beta$-hydroxyethyl)3,3,6,6-tetramethyl-piperazine-2-one;

$N^4$-($\beta$-hydroxyethyl)3,3-pentamethylene-5,5-dimethyl-piperazine-2-one;

$N^4$-($\beta$-hydroxyethyl)3,3,6-trimethyl-diazepin-2-one;

$N^4$-($\beta$-hydroxyethyl)3,3,6,6-tetramethyl-diazepin-2-one;

$N^4$-($\beta$-hydroxyethyl)3,3-pentamethylene-5,5-hexamethylene-diazepin-2-one;

$N^4$-($\beta$-hydroxyethyl)3,3-pentamethylene-diazepin-2-one;

$N^4$-($\beta$-hydroxyethyl)3,3,5,5,7,7-hexamethyl-diazepin-2-one;

$N^4$-($\beta$-hydroxyethyl)3,3-pentamethylene-5,5,7,7-tetramethyl-diazepin-2-one;

$N^4$-($\beta$-hydroxyethyl)3,3-dimethyl-5,5-pentamethylene-piperazin-2-one;

$N^4$-($\beta$-hydroxyethyl)3,3,6,6-tetraethyl-5,5-pentamethylene-diazepin-2-one;

$N^4$-($\beta$-hydroxyethyl)3,3-dimethyl-5,6-tetramethylene-diazepin-2-one;

$N^4$-($\beta$-hydroxyethyl)3,3,5,5-tetramethyl-6,7-tetramethylene-diazepin-2-one;

cis-3,3-dimethyl-decahydroquinoxalin-2-one;

cis-3,3-pentamethylene-decahydroquinoxalin-2-one;

cis-$N^1$-(3',5'-di-t-butyl-4-hydroxybenzyl)3,3-dimethyl-decahydroquinoxalin-2-one;

trans-$N^1$-(3',5'-di-t-butyl-4-hydroxybenzyl)3,3-dimethyl-decahydroquinoxalin-2-one;

1,4-butane-bis-[$N^1$-(3,3-dimethyl-decahydroquinoxalin-2-one)];

trans-1,6-hexanediol-bis-[$N^1$-(3,3-dimethyl-decahydroquinoxalin-2-one)di-carboxylate];

trans-1,6-hexanediol-bis[$N^1$-(3,3-pentamethylenedecahydroquinoxalin-2-one)dicarboxylate]; and, trans-$N^1$-carbobutoxy-3,3-dimethyl-decahydroquinoxalin-2-one.

Most preferred substituted mono-keto-1,4-diazaalkan-2-ones are:

$N^1$-dodecyl-3,3,5,5-tetramethyl-2-piperazinone;

$N^1$-t-octyl-3,3,5,5-tetramethyl-2-piperazinone;

1,2-ethane-bis-($N^1$-3,3,5,5-tetramethyl-2-piperazinone);

$N^4$-t-octyl-3,3,6,6-tetramethyl-2-piperazinone;

$N^1$-phenyl-3,3,5,5-tetramethyl-2-piperazinone;

$N^1$-t-butyl-3,3-dimethyl-5,5-pentamethylene-2-piperazinone;

$N^1$-butyl-3,3,5,5,7-pentamethyl-1,4-diazepin-2-one;

trans-3,3-pentamethylene-decahydroquinoxalin-2-one;

trans-3,3-dimethyl-decahydroquinoxalin-2-one;

trans-3,3-dimethyl-$N^4$-$\beta$-hydroxyethyl-decahydroquinoxalin-2-one;

trans $N^1$-dodecyl-3,3-dimethyl-decahydroquinoxalin-2-one;

trans-$N^1$-benzyl-3,3-dimethyl-decahydroquinoxalin-2-one;

trans-$N^1$-dodecyl-3,3-pentamethylene-decahydroquinoxalin-2-one;

trans-$N^1$-3,3-pentamethylene-decahydroquinoxalin-2-one; and, trans-3,3-dimethyl-$N^4$-$\beta$-hydroxylethyl-decahydroquinoxalin-2-one.

As will be evident, compositions of this invention include compounds in which the diaza ring has a fixed two-carbon bridge between the two two N atoms of the diaza ring, the remaining portion of the ring having a bridge of various length having two or more carbon atoms. More specifically, these compositions include 2-keto compounds having an $N^1$-adjacent carbonyl and two substituents, which may be cyclizable, on the $N^4$-adjacent carbon in the fixed two-carbon bridge. In addition, one or more C atoms of the variable bridge may be substituted with one or more substituents. When the substituents on the variable portion of the diaza ring are cyclizable, for example forming cyclohexyl, cis and trans isomers may be formed. Dimers and bis compounds of polysubstituted 2-keto-1,4-diazacycloalkanes can also be prepared as described hereinafter, and used as effective UV stabilizers.

Compositions of this invention are organic materials which have been stabilized to combat the deleterious effects of thermal, oxidative or actinic light such as are usually evidenced by discoloration and/or embrittlement. These materials can be low or high molecular weight materials, and particularly includes homopolymers, copolymers and mixtures thereof. Examples of materials that can be stabilized against degradation due to UV light are oils; monomers, particularly $\alpha,\beta$-olefinically unsaturated monomers such as acrylates, dienes, vinyl nitriles, and the like; and other lower molecular weight materials such as alcohols, aldehydes, and the like. Examples of known materials which can be stabilized with polysubstituted 2-keto diazacycloalkenes are natural rubber, synthetic rubbers such as cis-polyisoprene, styrene-butadiene rubber, diene-nitrile rubbers, polyepihalohydrin polymers, and the like, polyurethanes, PVC resins, ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The substituted 2-keto diazacycloalkanes can also be used to stabilize mixtures and blends of polymeric materials such as ABS resin blends, PVC and polymethacrylate blends, and blends of polyolefin homopolymers and copolymers such as blends of polypropylene and epdm polymers.

The substituted 2-keto diazacycloalkanes are particularly useful as UV stabilizers for normally solid polymers such as the poly-$\alpha$-monoolefin homopolymers of $\alpha$-olefins having up to 3 carbon atoms, e.g. ethylene-propylene and their copolymers; vinyl resins formed from the polymerization of vinyl halides or from copolymerization of vinyl halides with unsaturated polymerizable compounds, for example, vinyl esters, $\alpha,\beta$ unsaturated acids, $\alpha,\beta$ unsaturated esters and unsaturated hydrocarbons; polyurethanes such as are prepared from polyols and an organic polyisocyanate; polyamides such as polymethyleneterephthalates; polycarbonates such as those prepared from bisphenol-A and phosgene; polyacetals; polyethylene oxide, polyacrylics such as polyacrylonitrile; polyphenyleneoxides such as those prepared from 2,6-dimethylphenol and the like. The $\alpha$-monoolefin monomers used to prepare the latter polymers include ethylene, propylene, isobutylene, 1-butene, 1-pentene, 1-hexene, 4-methyl-1-pentene, and the like. Excellent results have been obtained using compounds of this invention, as well as known substituted 2-keto diazacycloalkanes to stabilize polypropylene against UV degradation.

The stabilized compositions of this invention are especially useful in those instances where the plastic article made from the stabilized composition is to be used outdoors, or indoors under intense actinic light.

Many known compounding ingredients may be used along with the substituted 2-keto diazacycloalkanes in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like; antioxidants such as 2,6-di-t-butyl paracresol, 2,2'-methylenebis-(4-ethyl-6-t-butylphenol), 2,2'-thiobis-(4-methyl-6-t-butylphenol), 2,2'-methylenebis-6-t-butyl-4-ethyl phenol, 4,4'-butylidenebis-(6-t-butyl-m-cresol), 2-(4-hydroxy-3,5-di-t-butylanilino)-4,6-bis(octylthio)-1,3,5-triazine, hexahydro-1,3,5-tris-$\beta$-(3,5-di-t-butyl-4-hydroxyphenyl) propionyl-s-triazine, tris-(3,5-di-t-butyl-4-hydroxybenzyl)isocyanurate, tetrakismethylene-3(3',5'-di-t-butyl-4'-hydroxyphenyl)propionate methane, distearyl thiodipropionate, dilauryl thiodipropionate, tri(nonylphenyl)phosphite, tin thioglycolate, and the like; and the other ingredients such as pigments, tackifiers, flame retardants, fungicides, and the like.

Compounding ingredients of particular interest to be used in the compositions of the invention are the antioxidant stabilizers. As the 2-ketodiazaalkane compounds of the invention are UV stabilizers, it is beneficial to add antioxidants to the compositions of the invention to achieve both UV light and oxygen stability of the compositions. The antioxidants are used in the range from about 0.1 part to about 10 parts by weight, preferably from about 0.2 to about 5 parts by weight per 100 parts by weight of the material. Of the types of antioxidants to be used are phosphate, sulfide and phenolic antioxidants, the last being preferred.

Examples of the phenolic antioxidants are 2,6-di-t-butylphenol; 2-methyl-4,6-dinonyl phenol; 2,6-di-t-butyl-p-cresol; 2,2'-methylbenebis(4-methyl-6-t-butyl phenol); 1,1'-methylenebis (2-naphthol); 4,4'-methylenebis(2,6-di-t-butyl phenol); 4,4'-thiobis(6-t-butyl-m-cresol); and the like. Although any phenolic antioxidant used in combination with the substituted 2-keto diazacycloalkanes would improve the heat and oxygen stability of the compositions the more preferred phenolic antioxidants are those having alkylhydroxyphenyl substituents on an ester or a heterocyclic nucleus.

Examples of phenolic antioxidants having alkylhydroxyphenyl substituents on an ester nucleus are compounds disclosed in U.S. Pat. No. 3,330,859 and disclosed in U.S. Pat. No. 3,627,725 and exemplified by di-lauryl $\alpha,\alpha$-bis(3,5-di-t-butyl-4-hydroxybenzyl)malonate; compounds exemplified by tetrakis (methylene-3-(3',5'-di-t-butyl-4'-hydroxyphenyl)propionate)methane; and the like.

Examples of phenolic antioxidant compounds having alkylhydroxyphenyl substituents on a heterocyclic nucleus are compounds where the heterocyclic nucleus is a triazine nucleus such as compounds disclosed in British Pat. No. 977,589 and exemplified by 2,4,6-tris(4-hydroxy-3,5-di-t-butyl benzylthio)-1,3,5-triazine; compounds disclosed in U.S. Pat. No. 3,706,740 an exemplified by 2,4,6-tris (3',5'-di-t-butyl-4'-hydroxybenzyl)-1,3,5-triazine; disclosed in U.S. Pat. No. 3,567,724 and exemplified by hexahydro-1,3,5-tris-$\beta$-(3,5-di-t-butyl-4-hydroxyphenyl)propionyl-s-triazine; disclosed in U.S. Pat. No. 3,694,440 and exemplified by 1,3,5-tris (4'-hydroxy-3',5'-di-t-butylphenylpropionyloxyethylthiopropionyl)hexahydro-1,3,5-triazine; and the like.

Examples of phenolic antioxidant compounds having alkylhydroxyphenyl substituents on an isocyanurate nucleus are compounds of the formula disclosed in U.S. Pat. No. 3,531,483 and exemplified by tris-(3,5-di-t- butyl-4-hydroxybenzyl) isocyanurate; disclosed in U.S. Pat. No. 3,678,047 and exemplified by 2,2',2"-tris(3-(3,5-di-t-butyl-4-hydroxyphenyl)propionyloxy)-ethyl isocyanurate; and the like.

Still other hindered phenols useful as thermal antioxidants are disclosed in U.S. Pat. No. 3,920,659, and in copending U.S. patent applications Ser. No. 697,345 and Ser. No. 697,387 which are incorporated herein by reference as if fully set forth.

The substituted 2-keto diazacyloalkane stabilizers, and the other compounding ingredients if used, can be admixed with substrates using known mixing techniques and equipment such as internal mixing kettles, a Banbury mixer, a Henschel mixer, a two-roll mill, an extruder mixer, or other standard equipment, to yield a composition which may be extruded, pressed, blow-molded or the like into film, fiber or shaped articles. Standard mixing times and temperatures can be employed. The objective is to obtain intimate and uniform mixing of the components. A favorable mixing procedure to use when adding the 2-keto-diazaalkane compound to a plastic material is to either dissolve or suspend the compound in a liquid such as hexane or benzene, add the plastic material in the form of a powder to the solution or suspension, evaporate off the liquid, and extruder mix the stabilized plastic material prior to forming the product.

The UV stability of a particular composition containing a polymeric material and a substituted 2-keto diazacycloalkane can be evaluated by exposing a prepared sample of the composition to Xenon or Carbon Arc light in a Weather-Ometer operating at a temperature, for example, of about 140° F. (60°C.). Degradation of the sample can be followed by periodically measuring the carbonyl absorption band at 1720 cm$^{-1}$ using an IR spectrophotometer. The rapid formation of carbonyl indicates failure of the sample. This test procedure is well known, and is published in the text Photodegradation, Photo-oxidation and Photostabilization of Polymers by Ranby and Rabek, John Wiley & Sons, N.Y., N.Y., (1975) at page 129 et seq. and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C.

The following examples are given to further illustrate the invention. Detailed procedures are set forth for the peparation of 2-keto diazacycloalkanes, particularly those of this invention, as is the preparation of sample compositions, and detailed test procedures and test results. Where not otherwise stated, parts are given as parts by weight and the temperatures are in degrees Centigrade. The relationship of parts by weight to parts by volume is that of grams to milliliters.

EXAMPLE 1

A. 3,3-dimethyl-decahydroquinoxalin-2-one is prepared as described by Bindler (U.S. Pat. No. 2,920,077) as follows:

17 parts of acetone cyanohydrin are added dropwise at room temperature to a solution of 22.8 parts of cis-1,2-diamino cyclohexane in 100 parts of water. The solution becomes cloudy and an oil is split off. After stirring for half an hour at room temperature, the dispersion is heated to 90°-95° and stirred for another 8 hours at room temperature while ammonia is evolved. The reaction solution is then evaporated to dryness under vacuum and a yellow residue is recrystallized from acetone. The compound melts at 165°-6° C. and is identified as 3,3-dimethyl-decahydroquinoxalin-2-one. 0.5 phr (parts per hundred parts resin) is blended into Hercules Profex 6501 polypropylene and extruded into film. The film is weathered in a Xenon Weather-O-Meter until initiation of decomposition which occurs at about 2000 hours (See Table I).

B. 3,3-dimethyl-decahydroquinoxalin-2-one is prepared as described by Hinsberg*, as follows:
*Hinsberg, Ann., 292, 245 (1896); ibid. 248, 71 (1888).

5.4 parts of o-phenylene diamine are placed in a flask and ethyl-2-bromoisobutyrate added thereto with ethanol solvent. The reaction mixture is heated and 3,3-dimethyl-3,4-dihydroquinoxalin-2-one is recovered. Upon hydrogenation in the presence of catalyst, 3,3-dimethyl-decahydroquinoxalin-2-one is formed which, when used at 0.5 phr concentration in polypropylene in a manner analogous to that set forth in Example 1A above, provides stabilization for about 2000 hours (see Table I).

C. 3,3-dimethyl-decahydroquinoxalin-2-one is prepared by a novel synthesis, more fully described in my U.S. Pat. No. 4,167,512, as follows:

5.4 parts of o-phenylenediamine and 40 parts chloroform are placed in a 250 ml flask, 20 parts 50% by weight NaOH solution is added followed by 0.5 part benzyl triethyl ammonium chloride (BTAC). The flask is cooled in an ice-bath and 5.5 parts acetone cyanohydrin in 10 parts chloroform are added dropwise over 30 minutes. The flask is cooled in the ice-bath for an additional two hours, then warmed and maintained at room temperature for another two hours. Conversion in excess of 90% is obtained. The reaction product is worked up, filtered and washed with CHCl$_3$ several times, and dried to yield 3,3-dimethyl-1,2,3,4-tetrahydroquinoxalin-2-one, which is dissolved in ethanol and conventionally hydrogenated.

EXAMPLE 2

1,4-diaza[3,3,5,5]-di-pentamethylene-2-one is prepared, starting with cyclohexanone, by cyclization of bis (1-cyanocyclohexyl)amine, reducing with aluminum hydride to form 1,4-diaze 3,3,5,5-dipentamethylene-2-imino, treating with acetic anhydride, and heating with hydrochloric acid, as stated hereinabove, and set forth in more detail in Monatshefto fur Chemie 106,1167-1173 (1975).

0.5 parts of the 1,4-diaza-[3,3,5,5]dipentamethylene-2-one prepared is blended into polypropylene, and the composition is formed into film and tested in a manner analogous to that described in Example 1. The tests indicate that the composition is UV stable for more than 1200 hours.

The structure of the known compound is:

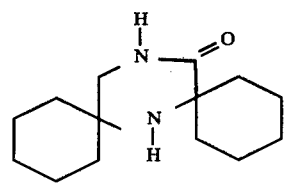

EXAMPLE 3

A. Preparation of 3,3,6-trimethyl-2-piperazinone

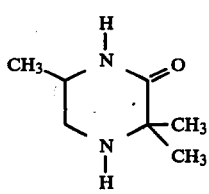

In a manner analogous to that described in U.S. Pat. No. 2,920,077, 148.3 g (2 moles) of 1,2-diaminopropane and about 500 ml water are placed in a 2-liter 3-necked flask. While stirring, 170.2 g (2 moles) of acetone cyanohydrin in 100 ml water are added in 20 min. The reaction is allowed to proceed at 80°–92° C. for 24 hr then water and unreacted materials are removed at 15 mm Hg. The residue, which formed a solid on standing, when dissolved in acetone and recrystallized was found to melt at 115°–117°.

Elemental Analysis Calculated: 55.35%C; 10.84%H; 21.52%N Analysis Found: 60.43%C; 10.09%H; 20.66%N The structure of the compound is supported by IR, NMR and mass spectrometer data. The error in elemental analysis found is attributable to the hygroscopicity of the compound.

In an analogous manner other dialkyl substituents may be made, for example, 3-hexyl-3,methyl-cis-decahydroquinoxalin-2-one.

B. Preparation of 4-(β-hydroxyethyl)-3,3,6-trimethyl-2-piperazinone

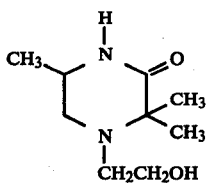

23.4 g (0.15 mole) of 3,3,6-trimethyl-2-piperazinone, prepared as described in example 3A above, about 100 ml ethanol and 7.3 g (0.165 mole) of ethylene oxide are charged to an autoclave and reacted at 163° C. for 6 hrs then cooled. Upon fractionation at reduced pressure a clear syrup, b.pt.198°–202° at 6.0 mm Hg, is obtained and identified as 4-(β-hydroxyethyl)3,3,6-trimethyl-2-piperazinone.

C. Preparation of 3,3,6,6-tetramethyl-2-piperazinone

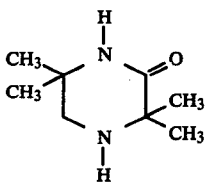

In a manner analogous to that described in example 3A above, 2,methyl-1,2-diaminopropane, water and acetone cyanohydrin are reacted, and the reaction product recovered. When dissolved in acetone and recrystallized it is identified as 3,3,6,6-tetramethyl-2-piperazinone.

Starting with preselected diamines and cyanohydrin derivatives, other desired substituents may be made in a similar manner. For example, 3,3-pentamethylene-6,6-diethyl-2-piperazinone; 3,3-pentamethylene-6,6-dimethyl-2-piperazinone; and the like may be prepared.

D. Preparation of $N^1$-propyl-3,3,6,6-tetramethyl-2-piperazinone

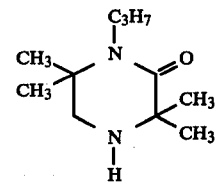

Substituents on the $N^1$ atom of the diaza ring may be made in the presence of base, such as sodium hydride, and the halide of the substituents to be made. For example, $N^1$-propyl-3,3,6,6-tetramethyl-2-piperazinone; $N^1$-isopropyl-3,3,6,6-tetramethyl-2-piperazinone; $N^1$-octyl-3,3,6,6-tetramethyl-2-piperazinone; $N^1$-octyl-3,3-pentamethylene-6,6-dimethyl-2-piperazinone; $N^1$-alkyl($C_{12}$–$C_{18}$)-3,3,6,6-tetramethyl-2piperazinone; $N^1$-alkyl($C_{12}$–$C_{18}$)-3,3-pentamethylene-6,6-dimethyl-2-piperazinone and the like are prepared in this manner.

E. Preparation of $N^4$-propyl-3,3,6,6-tetramethyl-2-piperazinone

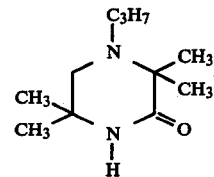

Substituents on the $N^4$ atom of the diaza ring may be made by heating with a halide of the desired substituent in a suitable solvent, forming the ammonium salt and then treating with sodium hydroxide to yield the desired $N^4$-substituted compound. For example, $N^4$-propyl-3,3,6,6-tetramethyl-2-piperazinone; $N^4$-octyl-3,3-pentamethylene-6,6-dimethyl-2-piperazinone; $N^4$-alkyl($C_{12}$–$C_{18}$)-3,3,6,6-tetramethyl-2-piperazinone; and the like are prepared in this manner.

F. Preparation of $N^4$-hydroxyalkyl-3,3,6,6-tetramethyl-2-piperazinone

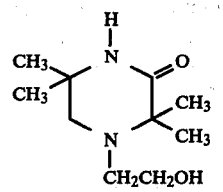

A β-hydroxyethyl substituent may be had on the $N^4$ atom of the diaza ring by heating with ethylene oxide in ethanol, as described in Example 3B hereinabove.

G. Preparation of 1,2-ethane-bis-(N¹-3,3,6,6-tetramethyl-2-piperazinone)

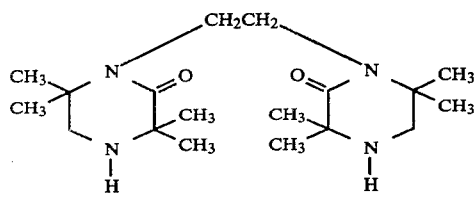

3,3,6,6-tetramethyl-2-piperazinone prepared as described in Example 3C hereinabove is heated with dibromoethane in the presence of sodium hydride to form the bis compound through N¹ represented hereinabove. The bis compound may be formed through the N⁴ atoms in the absence of base. Other bis compounds may be formed in an analgous manner.

When each of the polysubstituted 2-keto-diazaalkane compounds identified in Example 3A–C hereinabove is blended into polypropylene in an amount about 0.5 parts of compound per 100 parts substrate, it is found that the compositions exhibit excellent UV stability. These and other substituted 2-keto-diazaalkanes are particularly suitable for use in any substantially colorless organic substrate which is exposed to light. By substantially colorless is meant that the materials are substantially water white, or have only slight color, such that a darkening of the material is apparent to the naked eye, and consequently deemed undesirable. The stabilizers themselves are not necessarily water white, but are used in so low a concentration as to lend no discernible or objectionable color to the substrate.

EXAMPLE 4

A. Preparation of trans-3,3-dimethyl-1,4-decahydroquinoxalin-2-one

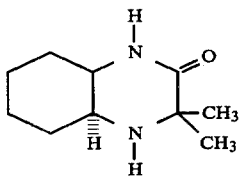

A mixture of cis and trans isomers of 1,2-diaminocyclohexane are dissolved in 500 ml water in a 3-necked flask, and acetone cyanohydrin was slowly added over a period of 45 mins. The mixture is stirred for an additional hour at room temperature, then warmed to 90°–95° C. and maintained at that temperature for 20 hrs. The reaction mixture is then cooled, filtered and the water is removed from the filtrate. Crystals obtained by recrystallization from acetone are found to be the trans isomer of 3,3-dimethyl-decahydroquinoxalin-2-one. The melting point of the crystals is about 218.5°–219.5° C.

Elemental analysis calculated: 65.9%C; 15.37%N; 9.95%H. Analysis found: 66.23%C; 15.53%N; 10.06%H.

B. Preparation of N¹-(benzyl)-trans-3,3-dimethyl-decahydroquinoxalin-2-one

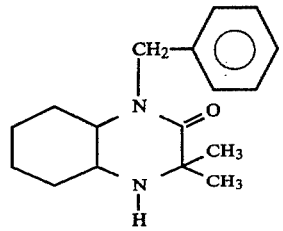

5.5 g sodium hydride (50% in oil) are placed in a 250 ml flask, 50 ml toluene are added, followed by 18.2 g of trans-3,3-di-methyl-1,4-decahydroquinoxalin-2-one.

The mixture is gradually brought to reflux under argon. Then 13.9 g benzyl chloride in 25 ml toluene are added dropwise in about half an hour, and the reaction mixture refluxed overnight. It is then cooled down and poured into 100 ml water, shaken and separated. The water layer is washed with ether and the combined organic layers dried over Na₂SO₄. After concentration and drying about 30.6 g of a white solid are obtained.

Elemental analysis calculated: 74.96%C; 10.28%N; 8.88%H Analysis found: 75%C; 10%N; 9.09:H The structure of the compound is supported by IR, NMR and mass spectrometer data.

C. In a manner analogous to that described in example 4B hereinabove a hindered phenol, preferably one which is antioxidant, may be substituted on the N¹-atom of the diaza ring.

D. In a manner analogous to that described in example 4B hereinabove, an alkyl substitutent may be substituted on the N¹-atom of the diaza ring, for example, with 1-bromobutane, a butyl substituent is obtained; with 1-bromododecane, a dodecyl substituent is obtained.

E. In a manner analogous to that described in example 4B hereinabove, N¹-carboalkoxylated compounds having from 2 to about 18 carbon atoms in the carboalkoxy group are prepared by reaction with chloroformates in the presence of base.

F. Preparation of 1,2-butane-bis-(N¹-trans-3,3-dimethyl-decahydroquinoxalin-2-one)

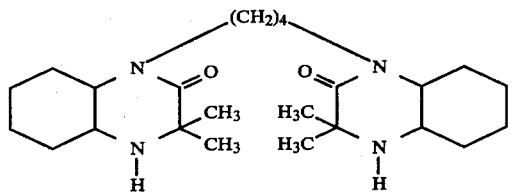

1.8 g sodium hydride (50% in oil) are placed in a 100 ml flask and 30 ml dried toluene added. After stirring under argon for 5 mins the toluene was pipetted away and 30 ml fresh dry toluene added, followed by 5.5 g trans-3,3-dimethyldecahydroquinoxalin-2-one. The mixture is heated to reflux under argon, while 3.6 g 1,4-dibromobutane in 10 ml toluene are added slowly. The reaction mixture was refluxed overnight, cooled, poured into 60 ml water and extracted with 100 ml benzene. The organic layer is dried over Na₂SO₄, filtered, and the solvent removed. The oil is triturated with hexane to give 2.5 g of a white solid which melts at 140°–4° C.

Elemental analysis calculated: 68.86%C; 13.38%N; 10.11%H Analysis found: 70.01%C; 12.44%N; 9.92%H.

The structure of the compound is confirmed by IR, NMR and mass spectrometer data.

In a manner analogous to the foregoing, other bis compounds may be prepared; for example, by reaction with α,α'-dibromo-p-xylene instead of dibromobutane, p-xylene-2,2'-bis-N$^1$-(3,3-dimethyl-decahydroquinoxalin-2-one) is prepared.

G. Preparation of trans-N$^4$-(β-hydroxyethyl)-3,3-dimethyl-decahydroquinoxalin-2-one

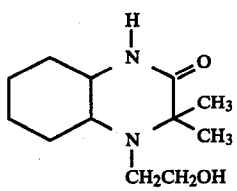

22.7 g of trans-3,3-dimethyl-decahydroquinoxalin-2-one and 6.1 g of ethylene oxide, preferably in the presence of an acid catalyst, are placed in an autoclave. The mixture is heated to about 220° C. for a couple of hours. The pressure is then dropped from 242 psi to 5 psi. The reaction is stopped, and the solid residue is triturated with benzene to give 21 g of an off-white solid which is purified by recrystallization from benzene-hexane or acetone to give a solid which melts at 152°-4° C.

Elemental analysis calculated: 63.69%C; 12.38%N; 9.80%H Analysis found: 62.46%C; 12.07%N; 9.58%H.

H. Preparation of N$^1$-dodecyl-trans-3,3-dimethyl-decahydroquinoxalin-2-one

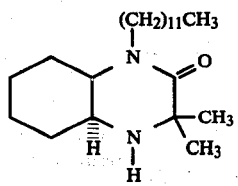

1.8 g sodium hydride (50% in oil) are placed in a 100 ml flask, and 30 ml toluene previously dried over molecular sieves, are added. To this mixture is added 5.5 g trans-3,3-dimethyl-1,4-decahydroquinoxalin-2-one, prepared as described hereinabove in Example 4A. The mixture is slowly warmed to reflux under argon and 8.23 g 1-bromododecane in 10 ml toluene was dripped in over a period of about an hour. After the addition the mixture was refluxed overnight, cooled down and poured into water. After extraction with benzene, the benzene solution is dried with Na$_2$SO$_4$, filtered and concentrated. The oil solidified upon standing. No solvent could be readily found to recrystallize the solid. When the solid is washed with pentane, almost all the color is removed. The solid has a m pt of 52°-59° C.

Elemental analysis calculated: 75.37%C; 7.99%N; 12.08H Analysis found: 76.47%C; 7.42% N; 12.39%H.

The structure of the compound is supported by IR, NMR and mass spectrometer data.

EXAMPLE 5

A. Preparation of cis and trans isomers of 3,3-pentamethylene-1,4-decahydroquinoxalin-2-one:

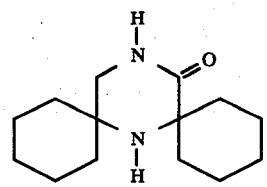

A mixture of 9.8 g cyclohexanone and 9.8 g sodium cyanide in 26 ml water was stirred at −15° C. in an ice-salt bath. A solution of 19.4 g sodium bisulfite in 43 ml water was added dropwise in 30 mins and the mixture vigorously stirred for an additional 4 hrs. The mixture is filtered and the filtrate extracted with ether. Upon removal of the ether 12 g crude oil is obtained, to which is added 11.4 g 1,2-diaminocyclohexane and 50 ml water. The mixture is stirred for 30 mins at room temperature, then warmed at about 90°-95° C. overnight. It is cooled, the solvent removed and the residue triturated with acetone to give 9 g pure white solid melting at 243.5°-244° C. Both isomers are formed, the cis isomer being soluble in acetone, while the trans is insoluble.

B. In a manner analogous to that described in Example 4B hereinabove, the 3,3-pentamethylene-1,4-decahydroquinoxalin-2-one obtained hereinbefore is reacted with benzyl chloride in the presence of sodium hydride in toluene, to form N$^1$-(benzyl)-3,3-pentamethylene-1,4-decahydroquinoxalin-2-one; and, if desired, a hindered phenol antioxidant may be substituted on the N$^1$-atom of the diaza ring in a similar manner.

C. In a manner analogous to that described in Example 4H hereinabove, trans-3,3-pentamethylene-1,4-decahydroquinoxalin-2-one obtained hereinabove is reacted with 1-bromododecane to yield N$^1$-dodecyl-trans-3,3-pentamethylene-1,4-decahydroquinoxalin-2-one.

EXAMPLE 6

Symmetrical N$^4$-adjacent C atoms may each be disubstituted, and primary, secondary and tertiary alkyl substituents may be had on the N$^1$ atom of the diaza ring as follows:

A. Preparation of N$^1$-propyl-3,3,5,5-tetramethyl-2-piperazinone

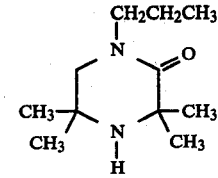

6.5 g of N$^1$-propyl-2-methyl-1,2-propanediamine was dissolved in 50 ml chloroform or bromoform in a 250 ml flask cooled in an ice-bath. 20 ml 50% by wt NaOH was added followed by 0.5 g benzyltriethylammonium chloride (BTAC). 5.5 g acetone cyanodryin was then added dropwise in 3 min. The ice was allowed to melt and the bath warmed slowly to room temperature. After about 5.5 hr the reaction mixture is filtered and washed thoroughly with chloroform. The combined chloroform solution was washed several times with 50 ml water, dried with sodium sulfate and concentrated. The oil was distilled at 117°–121° C. under 10 mm Hg to collect 4.6 g of a colorless oil. The structure of the compound is supported by IR, GC, NMR and mass spectrometer data.

B. In a manner analogous to that described immediately hereinabove, $N^1$-isopropyl3,3,5,5-tetramethyl-2-piperazinone represented by the structure

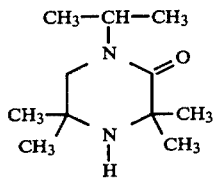

is prepared by placing 6.5 g of $N^1$-isopropyl2-methyl-1,2-propanediamine and 50 ml chloroform or bromoform in a flask cooled in an ice-bath, adding 20 ml NaOh and 0.5 g BTAC, followed by 5.5 g acetone cyanodydrin added slowly as before. The reaction mixture is worked up and distilled at 118°–121° C. under 10 mm Hg to yield 5.1 g of a colorless oil which solidified on standing. The solid melted at 82°–4° C.

C. The order of addition of NaOH and BTAC is changed, compared with that described immediately hereinabove, and $N^1$-t-octyl-3,3,5,5-tetramethyl-2-piperazinone represented by the structure

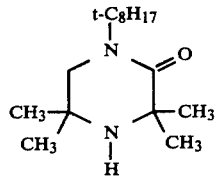

is prepared by placing 5.0 g $N^1$-t-octyl-2-methyl-1,2-propane diamine and 35 ml chloroform or bromoform in a 250 ml flask, adding 2.3 g acetone cyanodryin, then adding 12 ml 50% NaOh slowly. The reaction mixture is warmed slowly to room temperature, and it is stirred overnight. Water is added until all the solid is dissolved, and the aqueous layer is separated and extracted with 40 ml chlorform. The combined chloroform solutions are washed several times with water, dried and concentrated to yield about 7.0 g of an oil which when distilled at 101°–4° C. under 0.2 mm Hg provides 4.2 g of a yellow oil. The structure of this oil is confirmed by IR, GC, NMR and mass spectrometer data.

D. In a manner analogous to that described hereinabove in this example 6, $N^1$-dodecyl-3,3,5,5-tetramethyl-2-piperazinone represented by the structure

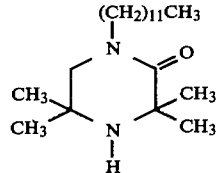

is prepared from N-dodecyl-2-methyl-1,2-propanediamine. The desired product is an oil which distills over at 145°–8° C. under 0.2 mm pressure. Any desired combination of one or more substituents may be had by an appropriate choice of diamine and cyanohydrin, and particularly, substituents may be had on one C atom which are together different from those on the other C atom.

E. In a manner analogous to that described hereinabove in this example 6, 1,2-ethane-bis-($N^1$-3,3,5,5-tetramethyl-2-piperazinone) represented by the structure

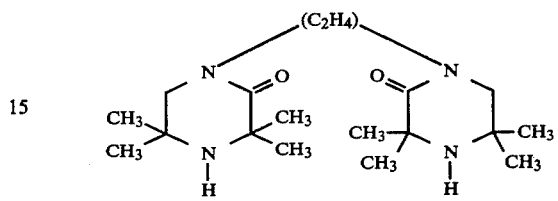

is prepared by placing 9.0 g N,$N^1$-(2-amino-2-methylpropyl)-ethylene diamine and 100 ml chloroform in a 500 ml flask, adding 11.4 g acetone cyanohydrin and 1.0 g BTAC. While stirring in an ice-bath, 30 ml 50% NaOH is added dropwise in 30 min. The reaction mixture is stirred overnight at room temperature, then water is added until all the solids are dissolved. The liquid layers are separated and the aqueous layer is extracted with 50 ml chloroform. The chloroform solutions are combined and washed with water several times, then dried and concentrated. Upon distillation at 155°–165° C. under 0.2 mm Hg an oil is obtained which, when triturated with hexanes, yields about 3 g of a light yellow solid having a m pt. 132°–4° C. The structure of the solid is confirmed by IR, GC, NMR and mass spectrometer data.

F. In a manner analogous to the foregoing, the following compounds are prepared: $N^1$-t-octyl-3,3-pentamethylene-5,5-dimethyl-2-piperazinone having a m pt 100°–2° C.; $N^1$-alkyl ($C_{12}$–$C_{18}$)-3,3,5,5-tetramethyl 2-piperazinone having a boiling pt in the range 115°–135° C. under 0.15 mm Hg: $N^1$-alkyl ($C_{12}$–$C_{18}$)-3,3-pentamethylene5,5-dimethyl-2-piperazinone having a b pt of 158°–169° C. under 0.25 mm; $N^1$-phenyl-3,3,5,5-tetramethyl-2-piperazinone having a pt 121°–6° C. under 0.15 mm Hg.

EXAMPLE 7

A. Primary, secondary and tertiary alkyl substituents may be had on both $N^1$ and $N^4$ atoms of the diaza ring, by first preparing the $N^1$-substituted compound as described in Example 6 hereinabove, and heating it with a halide of the desired substituent in a suitable solvent, forming the ammonium salt and then treating with sodium hydroxide to yield the desired $N^4$-substituted compound. Thus any desired combination of primary, secondary and tertiary alkyl substituents may be provided on the $N^1$ and $N^4$ atoms of the diaza ring. For example, $N^1$-propyl-$N^4$-isopropyl-3,3,5,5-tetramethyl-2-piperazinone; $N^1$-isopropyl-$N^4$-t-octyl-3,3,5,5-tetramethyl-2-piperazinone; $N^1$-$N^4$-bis[(t-octyl)-3,3,5,5-tetramethyl-2-piperazinone]; and the like may be prepared.

B. A β-hydroxyethyl substituent may be had on the $N^4$ atom of the diaza ring by heating with ethylene oxide in ethanol, as described in Example 3B hereinabove.

EXAMPLE 8

A. Preparation of 3,3,7,7-tetramethyl-1,4-diazepin-2-one

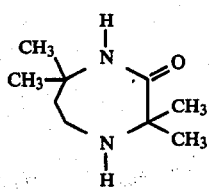

In a manner analogous to that described in Example 3C hereinabove, 3-methyl-1,3-diaminobutane, water and acetone cyanohydrin are reacted, and the reaction product recovered. When dissolved and recrystallized from acetone it is identified as 3,3,7,7-tetramethyl-1,4-diazepin-2-one. Other primary amines may be used for other substituents.

B. Preparation of $N^1$-(butyl)-3,3,5,5,7-pentamethyl-1,4-diazepin-2-one.

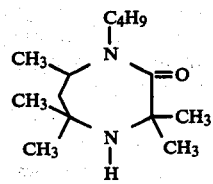

In a manner analogous to that described in Example 1C hereinabove $N^1$-butyl-4-methyl-2,4-pentanediamine and acetone cyanohydrin are reacted in the presence of 50% NaOH and a quaternary ammonium chloride catalyst such as BTAC, in a chloroform of bromoform solvent medium. The flask is kept in an ice-bath and gradually allowed to warm until the reaction is complete. Excellent conversion is had; the above structure of the compound is confirmed by IR, NMR and mass spectrometer data. Any desired $N^1$ substitution may thus be effected by reaction with an appropriately substituted $N^1$-4-methyl-2,4-pentanediamine.

C. Preparation of $N^1$-(butyl)-$N^4$-(propyl)-3,3,5,5,7-pentamethyl-1,4-diazepin-2-one

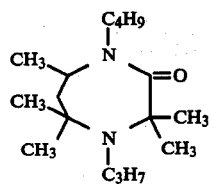

In a manner analogous to that described in Example 3E hereinabove, the desired $N^4$ substitution is made by reacting a halide of the desired substituent in a suitable solvent medium, forming the ammonium salt and then treating with sodium hydroxide. Accordingly, $N^1$-(butyl)-3,3,5,5,7-pentamethyl-1,4-diazepin-2-one is heated with 1-chloropropane and worked up to yield $N^1$(butyl)-$N^4$-(propyl)-3,3,5,5,7-pentamethyl-1,4-diazepin-2-one.

In a manner analogous to that described in Example 3F hereinabove, a-hydroxyethyl substituent may be had on the $N^4$ atom of the diaze ring, by heating with ethylene oxide in ethanol.

EXAMPLE 9

Preparation of $N^1$-t-octyl-3,3-pentamethylene-5,5-diamethyl-2-piperazinone-$N^4$-oxyl

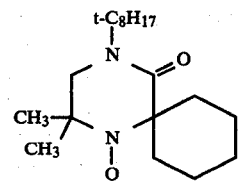

3.08 g (1 equivalent) of $N^1$-t-octyl-3,3-pentamethylene-5,5-dimethyl-2-piperazinone and 50 ml dichloromethane were placed in a 250 ml flask. 4.06 g (2 equivalents) m-chloroperbenzoic acid was added in small portions during a 20 min period. After 6 hrs, dichloromethane was added until all solid went into solution, then washed 4 times with 60 ml aliquots of 5% sodium carbonate solution. The organic layer was dried over sodium sulfate and concentrated. The oil solidified and was recrystallized from pentane. Orange-colored crystals were collected. The structure of the solid is confirmed by IR, GC, NMR and mass spectrometer data. Other substituents are introduced in an analogous manner to yield other nitroxy compounds.

A hydroxyl radical may be substituted for hydrogen on the $N^4$ atom of the diaza ring in a manner similar to that described immediately hereinabove, except that only one equivalent of m-chloroperbenzoic acid is used. Thus starting with 1 equiv of $N^1$-isopropyl-3,5,5,-trimethyl-3-isobutyl-2-piperazinone and 2 equivs of m-chloroperbenzoic acid, we obtain 3-isobutyl-$N^4$-hydroxy-$N^1$-isopropyl-3,5,5-trimethyl-2-piperazinone.

The following Table I sets forth data obtained on tests with 20 mil thickness polypropylene samples. All samples contain 0.5 parts stabilizer per 100 parts resin (phr) and also include 0.25 phr of Irganox 1010 antioxidant.

TABLE I

| Example | UV stabilizer additive | Xenon Weatherometer Hours |
|---|---|---|
| | NONE | 750 |
| | Tinuvin<sup>R</sup>327; 2-(3',5'-di-t-butyl-2'-hydroxyphenyl-5-chloro-benzotriazole | 1250 |
| 4A | trans-3,3-dimethyl-decahydroquinoxalin-2-one | 4000 |
| 4A | cis-3,3-dimethyl-decahydroquinoxalin-2-one | 2000 |
| 4G | trans-$N^4$-($\beta$-hydroxyethyl)-3,3-dimethyl-decahydroquinoxalin-2-one | 4000 |
| 5A | trans-3,3-pentamethylene-decahydro-quinoxalin-2-one | 5500 |
| 3A | 3,3,6-trimethyl-2-piperazinone | ≈ 1500 |
| 3B | 4-($\beta$-hydroxyethyl)-3,3,6-trimethyl-2-piperazinone | ≈ 1500 |
| 3C | 3,3,6,6-tetramethyl-2-piperazinone | ≈ 1500 |
| 3D | $N^1$—propyl-3,3,6,6-tetramethyl-2-piperazinone | ≈ 1500 |
| 3E | $N^4$—propyl-3,3,6,6-tetramethyl-2-piperazinone | ≈ 1500 |
| 3F | $N^4$—hydroxyethyl-3,3,6,6-tetramethyl-2-piperazinone | ≈ 1500 |
| 3G | 1,2-ethane-bis-($N^1$—3,3,6,6-tetramethyl-2-piperazinone | ≈ 1500 |
| 4B | $N^1$—(benzyl-trans-3,3-dimethyl-decahydroquinoxalin-2-one | ≈ 4000 |
| 4F | 1,2-butane-bis-($N^1$—trans-3,3-dimethyl-decahydroquinoxalin-2-one) | ≈ 4000 |
| 4G | trans-$N^4$—($\beta$-hydroxyethyl)-3,3-dimethyl- | ≈ 4000 |

TABLE I-continued

| Example | UV stabilizer additive | Xenon Weatherometer Hours |
|---|---|---|
| | decahydroquinoxalin-2-one | |

*Stabilizer prepared in a manner analogous to that described in the Example referred to, and set forth hereinabove.

The following Table II sets forth data obtained on tests with 10 ml thickness polypropylene samples. All samples contain 0.5 parts stabilizer per 100 parts resin (phr) and also include 0.25 phr of Irganox 1010 antioxidant.

TABLE II

| Example* | UV stabilizer additive | Xenon Weatherometer Hours |
|---|---|---|
| | NONE | 560 |
| | Tinuvin$^R$327 | 1425 |
| 3G | 1,8-octanedioic-bis($N^1$—3,3-dimethyl-2-piperazinone) | 1200 |
| 4F | 1,2-butane-bis-($N^1$—trans-3,3-dimethyl-decahydroquinoxalin-2-one | 1770 |
| 4H | $N^1$—dodecyl-trans-3,3-dimethyl-decahydro-quinoxalin-2-one | 1860 |
| 5C** | $N^1$—dodecyl-trans-3,3-pentamethylene-1,4-decahydroquinoxalin-2-one | 2000 |
| 6C** | $N^1$—t-octyl-3,3,5,5-tetramethyl-2-piperazinone | >2000 |
| 6D | $N^1$—dodecyl-3,3,5,5-tetramethyl-2-piperazinone | >2000 |
| 6E** | 1,2-ethane-bis-($N^1$—3,3,5,5-tetramethyl-2-piperazinone | >2000 |
| 8** | $N^1$—t-octyl-3,3-pentamethylene-5,5-dimethyl-2-piperazinone-$N^4$—oxyl | >2000 |

*Stabilizer prepared in a manner analogous to that described in the Example referred to, and set forth hereinabove.
D**Still being tested.

We claim:

1. A bis compound represented by the formula

M'—X—M"

wherein M' and M" represents two 2-keto-1,4-diazacycloalkane moieties connected through each 1-position of each moiety, or each 4-position of each moiety via a bivalent radical X selected from the group consisting of bivalent alkyl having from 1 to 24 carbon atoms, and the structure

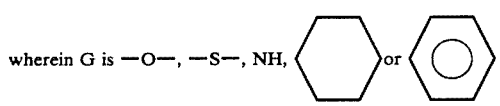

wherein G is —O—, —S—, NH, and y and z are individually an integer from 1 to about 6; and, wherein M' and M" represent polysubstituted 2-keto-1,4-diazacycloalkanes having a fixed two-carbon bridge between the $N^1$ and $N^4$ atoms of the diaza ring having a structural formula selected from

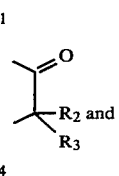

wherein, $R_1$ and $R_4$ independently represent hydrogen, alkyl having from 1 to 24 carbon atoms, hydroxyalkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms;

$R_4$ optionally also represents oxygen, hydroxy or alkoxy having from 1 to 8 carbon atoms;

$R_2$ and $R_3$ independently represent alkyl having from 1 to 12 carbon atoms, haloalkyl having from 1 to 12 carbon atoms, cyanoalkyl having from 2 to 12 carbon atoms, aminoalkyl having from 1 to 12 carbon atoms, cycloalkyl having from 5 to 14 carbon atoms, hydroxy-cycloalkyl having from 5 to 14 carbon atoms, alkenyl having from 2 to 14 carbon atoms, and unsubstituted hydrocarbon aralkyl having from 7 to 14 carbon atoms; and, $R_5$ represents alkyl having from 1 to 12 carbon atoms, hydroxyalkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms.

2. A bis compound represented by the formula

M'''—X—M'''' wherein M''' and M'''' represent two 2-keto-1,4-diazacycloalkane moieties connected through each 1-position of each moiety, or each 4-position of each moiety via a bivalent radical X selected from the group consisting of bivalent alkyl having from 1 to 24 carbon atoms, and the structure

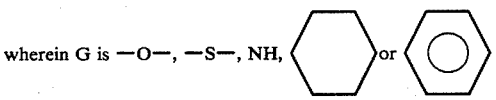

wherein G is —O—, —S—, NH, and y and z are individually an integer from 1 to about 6; and, wherein M''' and M'''' represent polysubstituted 2-keto-1,4-diazacycloalkanes having a fixed two-carbon bridge between the $N^1$ and $N^4$ atoms of the diaza ring having a structural formula selected from

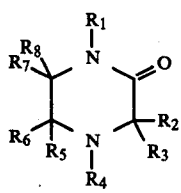 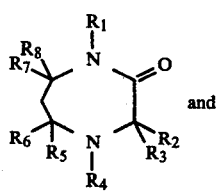

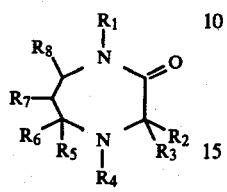

wherein,

R₁ and R₄ independently represent hydrogen, alkyl having from 1 to 24 carbon atoms, hydroxyalkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms;

R₄ optionally also represents oxygen, hydroxy or alkoxy having from 1 to 8 carbon atoms;

R₂ and R₃ independently represent alkyl having from 1 to 12 carbon atoms, haloalkyl having from 1 to 12 carbon atoms, cyanoalkyl having from 2 to 12 carbon atoms, aminoalkyl having from 1 to 12 carbon atoms, cycloalkyl having from 5 to 14 carbon atoms, hydroxy-cycloalkyl having from 5 to 14 carbon atoms, alkenyl having from 2 to 14 carbon atoms, and unsubstituted hydrocarbon aralkyl having from 7 to 14 carbon atoms;

R₅, R₆, R⁷, R₈ independently represent alkyl having from 1 to 12 carbon atoms, hydroxyalkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms;

R₇, R₈ additionally also represent hydrogen; and,

R₅, R₆ may when taken together with the carbon atom to which they are attached, form an alkylene ring or a pyridine ring.

3. The polysubstituted 2-keto-1,4-diazacycloalkanes of claim 1 wherein hydrogen atoms common to fused rings of said bicyclic mono-keto compound are transpositioned.

4. A polysubstituted compound of claim 1 selected from the group consisting of
trans-3,3-pentamethylene-decahydroquinoxalin-2-one;
trans-3,3-dimethyl-decahydroquinoxalin-2-one;
trans-3,3-dimethyl-N⁴-β-hydroxyethyl-decahydroquinoxalin-2-one;
trans-N¹-dodecyl-3,3-dimethyl-decahydroquinoxalin-2-one;
trans-N¹-benzyl-3,3-dimethyl-decahydroquinoxalin-2-one;
trans-N¹-3,3-pentamethylene-decahydroquinoxalin-2-one; and,
trans-3,3-dimethyl-N⁴-β-hydroxyethyl-decahydroquinoxalin-2-one.

5. A polysubstituted compound of claim 2 selected from the group consisting of
1,2-ethane-bis-(N¹-3,3,5,5-tetramethyl-2-piperazinone;
o-phenylene-bis-N¹-(3,3,5,5-tetramethyl-2-piperazinone);
trans-1,2-cyclohexane-bis-N¹-(3,3,5,5-tetramethyl-2-piperazinone); and,
trans-1,2-cyclohexane-bis-N¹-(3,5,5-trimethyl-3-isoamyl-2-piperazinone).

* * * * *

UNITED STATES PATENT AND TRADEMARK OFFICE
CERTIFICATE OF CORRECTION

PATENT NO. : 4,466,916
DATED : August 21, 1984
INVENTOR(S) : JOHN T. LAI and PYONG-NAE SON It is certified that error appears in the above-identified patent and that said Letters Patent are hereby corrected as shown below:

Column 25, line 38 "$R^7$" should read --$R_7$--.

$\mathfrak{Signed}$ and $\mathfrak{Sealed}$ this

Thirtieth Day of July 1985

[SEAL]

Attest:

DONALD J. QUIGG

Attesting Officer     Acting Commissioner of Patents and Trademarks